(12) United States Patent
Huang

(10) Patent No.: US 9,435,761 B2
(45) Date of Patent: Sep. 6, 2016

(54) ELECTROCHEMICAL STRIP AND MANUFACTURING METHOD THEREOF

(71) Applicant: YUTEK TRONIC INC., New Taipei (TW)

(72) Inventor: Chuan-Hsing Huang, Taipei (TW)

(73) Assignee: YUTEK TRONIC INC., New Taipei (TW)

( * ) Notice: Subject to any disclaimer, the term of this patent is extended or adjusted under 35 U.S.C. 154(b) by 0 days.

(21) Appl. No.: 14/506,378

(22) Filed: Oct. 3, 2014

(65) Prior Publication Data
US 2015/0021179 A1   Jan. 22, 2015

Related U.S. Application Data

(63) Continuation-in-part of application No. 13/444,065, filed on Apr. 11, 2012, now abandoned.

(51) Int. Cl.
| | |
|---|---|
| *G01N 27/327* | (2006.01) |
| *G01N 27/30* | (2006.01) |
| *C23C 18/24* | (2006.01) |
| *C23C 18/32* | (2006.01) |
| *C23C 18/42* | (2006.01) |
| *C23C 18/31* | (2006.01) |
| *C23C 18/16* | (2006.01) |

(52) U.S. Cl.
CPC .......... *G01N 27/307* (2013.01); *C23C 18/1641* (2013.01); *C23C 18/1651* (2013.01); *C23C 18/24* (2013.01); *C23C 18/31* (2013.01); *C23C 18/32* (2013.01); *C23C 18/42* (2013.01); *G01N 27/327* (2013.01); *G01N 27/3272* (2013.01)

(58) Field of Classification Search
CPC .......... G01N 27/327–27/3272; G01N 27/307; G01N 27/333
See application file for complete search history.

(56) References Cited

U.S. PATENT DOCUMENTS

| | | |
|---|---|---|
| 6,429,043 B1 | 8/2002 | Nakazawa et al. |
| 2011/0051387 A1 | 3/2011 | Tachibana et al. |
| 2011/0139491 A1 | 6/2011 | Chang |
| 2011/0180764 A1 | 7/2011 | Takahashi et al. |
| 2012/0183679 A1 | 7/2012 | Chen |

*Primary Examiner* — Alexander Noguerola
(74) *Attorney, Agent, or Firm* — Ming Chow; Sinorica, LLC

(57) ABSTRACT

An electrochemical strip is disclosed. The electrochemical strip includes a substrate and an electrode deposited on the substrate. The electrode includes a conductive paste layer, a first metal layer, a second metal layer, a third metal layer, and a fourth metal layer. The conductive paste is made of a material selected from the group consisting of copper paste, nickel paste, silver paste, and silver-carbon paste. The first metal layer is made of a group VIII metal. The second metal layer is made of nickel. The third metal layer is made of a group VIII metal. The fourth metal layer is made of a material selected from the group consisting of palladium, gold, and platinum.

10 Claims, 11 Drawing Sheets

ELECTROCHEMICAL STRIP AND MANUFACTURING METHOD THEREOF

CROSS-REFERENCE TO THE RELATED APPLICATION

This application is a Continuation in-part of U.S. patent application Ser. No. 13/444,065 entitled "ELECTROCHEMICAL STRIP AND MANUFACTURING METHOD THEREOF" filed on Apr. 11, 2012.

BACKGROUND OF THE INVENTION

1. Technical Field

The present invention relates to an electrochemical strip, and more particularly to an electrochemical strip for bio-test.

2. Description of Related Art

The development of the mechanical and electrical technology facilitates detection of biological samples via electrochemical or optical methods. By employing electrochemical method, for example, blood sugar can be detected via redox reaction that occurs when glucose in blood sample reacts with glucose oxidase (GOD) coated on the test strip. Specifically, an electric signal produced by redox reaction is used to detect the content of glucose participated in the response, and the signal can be converted to the concentration of blood sugar. By employing optical method, a reaction occurred between glucose and enzyme results in changing of color in test strip, then the change of color is detected and converted to concentration of blood sugar via colorimetric method.

Recently, an electrochemical strip is employed increasingly. Since the strip needs to detect an electric current signal produced by the electrochemical reaction, the strip needs to have a conductive electrode to receive the signal and transmit the signal to a measuring instrument for conversion. According to the techniques well known to those skilled in the art, the conductive electrode is usually made by plating nickel (Ni) and palladium (Pd) on a copper electrode or coating active-carbon layer on a silver paste. However, the general cost of electro-deposing nickel and palladium on a copper electrode is high. On the other hand, there is a method to form the electrode by directly disposing an inert group metal such as gold, platinum, and palladium on a substrate via vapor-deposition or sputtering-deposition, and then eliminating the unnecessary part via etching to keep the necessary parts only. However, this method results in serious material consumption and high manufacturing cost. Additionally, one may manufacture the electrode by coating an active-carbon layer on printed silver paste circuits to reduce the cost. Nevertheless, the manufactured electrodes have worse accuracy and stability in measurement than the electrodes made via the vapor-deposition or sputtering-deposition and which will consumes extra cost in quality control.

SUMMARY OF THE INVENTION

In an attempt to overcome the recited defects of the existing test strips, the present invention provides an electrochemical strip including a substrate and an electrode disposed on the substrate. The electrode includes a conductive paste layer, a first metal layer, a second metal layer, a third metal layer, and a fourth metal layer. The first metal layer is made of a group VIII metal. The second metal layer is made of nickel (Ni). The third metal layer is made of a group VIII metal. The fourth metal layer is made of a metal selected from the group consisting of palladium (Pd), gold (Au), and platinum (Pt).

An objective of the present invention is to provide an electrochemical strip including printed conductive paste and thus facilitate the production of a bio-test strip and effectively reduce the manufacturing cost.

Another objective of the present invention is to provide an electrochemical strip including palladium (Pd) as the material of the nickel layer, thus effectively prevents leaking of nickel (Ni) and is contributive to the disposition of the following layers.

Still another objective of the present invention is to provide an electrochemical strip including palladium (Pd), gold (Au), or platinum (Pt) as the material in the outer layer of the electrode, thus effectively increases sensitivity and specificity of the test.

In addition, the present invention provides an electrochemical strip including a substrate and an electrode disposed on the substrate. The electrode includes a conductive paste layer, a first metal layer, a second metal layer, a third metal layer, and a fourth metal layer. The conductive paste layer is made of a material selected from the group consisting of copper paste, nickel paste, silver paste, and silver-carbon paste. Furthermore, the conductive paste layer is printed on the substrate, and then is roughened by etching. The first metal layer, which is made of a group VIII metal, is chemically plated on the conductive paste layer. The second metal layer, which is made of nickel, is chemically plated on the first metal layer. The third metal layer, which is made of a group VIII metal, is chemically plated on the second metal layer. The fourth metal layer, which is made of a metal selected from the group consisting of palladium (Pd), gold (Au), or platinum (Pt), is chemically plated on the third metal layer.

An objective of the present invention is to provide an electrochemical strip including printed conductive paste and thus facilitates the production of a bio-test strip and effectively reduces the manufacturing cost.

Another objective of the present invention is to provide an electrochemical strip including palladium (Pd) as the outer layer material of the nickel layer, thus effectively prevents leaking of nickel (Ni) and is contributive to the disposition of the following layers.

Still another objective of the present invention is to provide an electrochemical strip including palladium (Pd), gold (Au), or platinum (Pt) as the material in the outer layer of the electrode, thus effectively increases sensitivity and specificity of the test.

Otherwise, the present invention provides an electrochemical strip including a substrate, an electrode and a carbon layer disposed on the substrate. The electrode includes a conductive paste layer, a first metal layer, a second metal layer, a third metal layer, and a fourth metal layer. The conductive paste layer is made of a material selected from the group consisting of copper paste, nickel paste, silver paste, and silver-carbon paste. In addition, the conductive paste layer and the carbon layer are printed on the substrate sequentially, and then the conductive paste layer is roughened by etching. Regarding the electrode, the first metal layer is made of a group VIII metal and chemically plated on the conductive paste layer; the second metal layer is made of nickel and chemically plated on the first metal layer; the third metal layer is made of a group VIII metal and chemically plated on the second metal layer; and the fourth metal layer is made of a metal selected from the group consisting of palladium (Pd), gold (Au), or platinum (Pt) and chemically plated on the third metal layer.

A primary objective of the present invention is to provide an electrochemical strip including printed conductive paste, which is characterized by excellent effect of screen printing and promoting the subsequent electrochemical plating of the electrode, thereby facilitating the production of a bio-test strip and effectively reducing the manufacturing cost.

Another objective of the present invention is to provide an electrochemical strip including a carbon layer with good conductivity printed partly on the conductive paste layer and displacing the insulating layer, thus effectively reducing the use of above-mentioned metals and achieving the purposes of lowering the manufacturing cost as well as complying with the requirements of environmental protection.

A further objective of the present invention is to provide an electrochemical strip including palladium (Pd) as the outer layer material of the nickel layer, thus effectively prevents leaking of nickel (Ni) and is contributive to the disposition of the following layers.

Still another objective of the present invention is to provide an electrochemical strip including palladium (Pd), gold (Au), or platinum (Pt) as the material in the outer layer of the electrode, thus effectively increases sensitivity and specificity of the test.

BRIEF DESCRIPTION OF THE DRAWINGS

The invention as well as a preferred mode of use, further objectives and advantages thereof will be best understood by reference to the following detailed description of illustrative embodiments when read in conjunction with the accompanied drawings, wherein.

DETAILED DESCRIPTION OF THE PREFERRED EMBODIMENTS

As mentioned above, the invention provides a solution to the problem that a typical strip for bio-test may encounter. The embodiments of the invention will be described herein below with reference to the accompanying drawings.

Figure 1A:
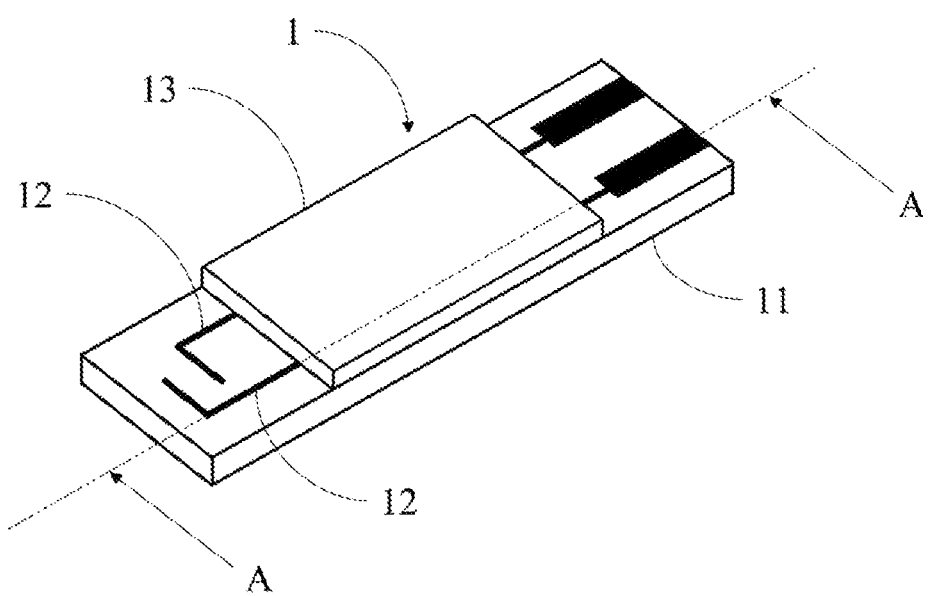
FIG. 1A is a schematic diagram representing an electrochemical strip according to a first embodiment of the present invention.

Referring to FIG. 1A, the electrochemical strip 1 according to a first embodiment of the invention includes a substrate 11, an electrode 12 disposed on the substrate 11, and an insulating layer 13 disposed on the electrode 12. The material used for the substrate 11 can be bio-inert plastic such as polyethylene terephthalate (PET), polycarbonate (PC), polyimide, glass fiber or phenolic resin.

Figure 1B:
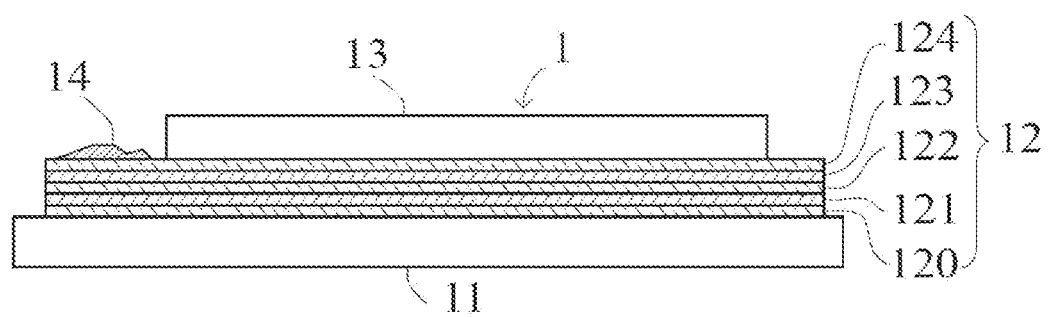
FIG. 1B is a cross-sectional view taken along A-A line of FIG. 1A, showing the electrochemical strip according to the first embodiment of the present invention.

Referring to FIG. 1B, the electrode 12 includes several layers serially stacked on the substrate 11. These layers are a conductive paste layer 120, a first metal layer 121, a second metal layer 122, a third metal layer 123, and a fourth metal layer 124. The first metal layer 121, the second metal layer 122, the third metal layer 123, and the fourth metal layer 124 are disposed via chemical plating.

The conductive paste layer 120 is a layer disposed on the substrate 11 via printing and is made of a material selected from the group consisting of copper paste, nickel paste, silver paste, and silver-carbon paste. Furthermore, the substrate 11 with the conductive paste layer 120 is etched by using plasma to eliminate the debris of the conductive paste layer 120 after the conductive paste layer 120 is printed on the substrate 11, and then the surface of the conductive paste layer 120 is activated by acid-washing.

Etching and acid-washing mentioned above are contributive to the following disposition of the first metal layer 121, the second metal layer 122, the third metal layer 123, and the fourth metal layer 124. Moreover, the thickness of the printed conductive paste layer 120 influences the chemical plating effect of the first metal layer 121.

In addition, the resin material used in the conductive paste layer 120 is the same with that used in the substrate 11. For example, the resin material used in the conductive paste layer 120 and for the substrate 11 is PET. As a result, the chemical plating effect of the first metal layer 121 becomes much better.

The first metal layer 121, which is made of a group VIII metal such as nickel (Ni), palladium (Pd), and platinum (Pt), is chemically plated on the conductive paste layer 120, and palladium (Pd) is preferably used for chemically plating the following second metal layer 122.

The second metal layer 122, which is made of nickel, is preferably used for chemically plating on the first metal layer 121. The third metal layer 123, which is made of a group VIII metal, is chemically plated on the second metal layer 122.

The fourth metal layer 124 is made of a group metal with good conductivity such as palladium (Pd), gold (Au), and platinum (Pt). It is preferably to use palladium (Pd) to form the fourth metal layer 124 for that a best accuracy of measurement could be obtained and that palladium (Pd) is a catalyst to facilitate electrochemical reaction. In this way, the electrons resulted from the electrochemical reaction could smoothly move within the electrode 12, and which benefits measurement of signals and evaluation of the corresponding concentration of an unknown sample to be tested via the electrochemical strip 1.

However, introducing gold (Au) as the material of the fourth metal layer 124 can be an alternative choice when considering the high cost of palladium (Pd).

Figure 3:
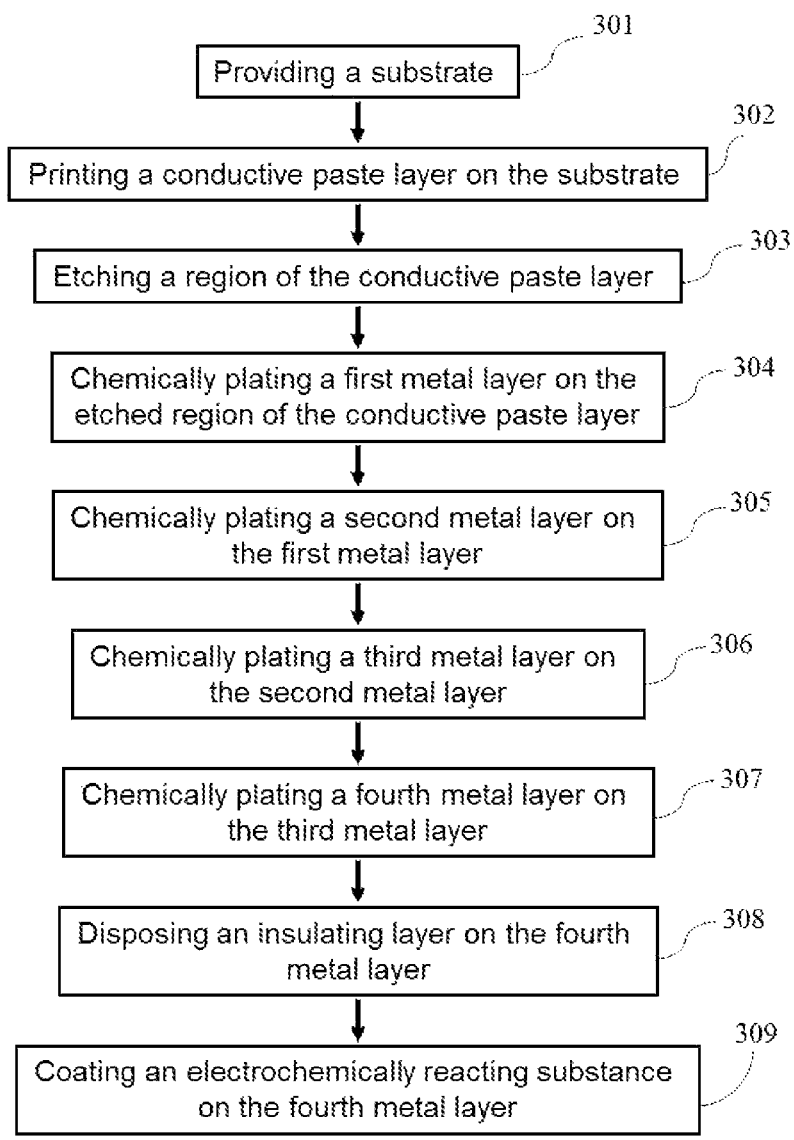
FIG. 3 is a flow chart illustrating steps of a manufacturing method of an electrochemical strip according to a first embodiment of the present invention.

Referring to FIG. 3, a manufacturing method of the electrochemical strip 1 according to the first embodiment of the present invention includes the following steps:

Step 301: Providing a substrate 11. The material used for the substrate 11 can be bio-inert plastic such as polyethylene terephthalate (PET), polycarbonate (PC), polyimide, glass fiber or phenolic resin.

Step 302: Disposing an electrode layer 12 on the substrate 11, including the step of printing a conductive paste layer 120 on the substrate 11. The conductive paste layer 120 is made of a material selected from the group consisting of copper paste, nickel paste, silver paste, and silver-carbon paste.

Step 303: Etching a region of the conductive paste layer 120, wherein the substrate 11 with the conductive paste layer 120 is etched by using plasma to eliminate the debris of the conductive paste layer 120, and then the surface of the conductive paste layer 120 is activated by acid-washing.

Step 304: Chemically plating a first metal layer 121 on the etched region of the conductive paste layer 120, wherein the first metal layer 121 is made of a group VIII metal.

Step 305: Chemically plating a second metal layer 122 on the first metal layer 121, wherein the second metal layer 122 is made of nickel (Ni).

Step 306: Chemically plating a third metal layer 123 on the second metal layer 122, wherein the third metal layer 123 is made of a group VIII metal.

Step 307: Chemically plating a fourth metal layer 124 on the third metal layer 123, wherein the fourth metal layer 124 is made of a material selected from the group consisting of palladium (Pd), gold (Au) and platinum (Pt).

Step 308: Disposing an insulating layer 13 on the fourth metal layer 124.

Step 309: Coating an electrochemically reacting substance 14 on the fourth metal layer 124.

In the first embodiment mentioned above, the whole electrode 12 is plated with the first metal layer 121, the second metal layer 122, the third metal layer 123, and the fourth metal layer 124. Otherwise, users can determine the layering structure of the electrode 12 according to the actual situation.

Figure 2A:
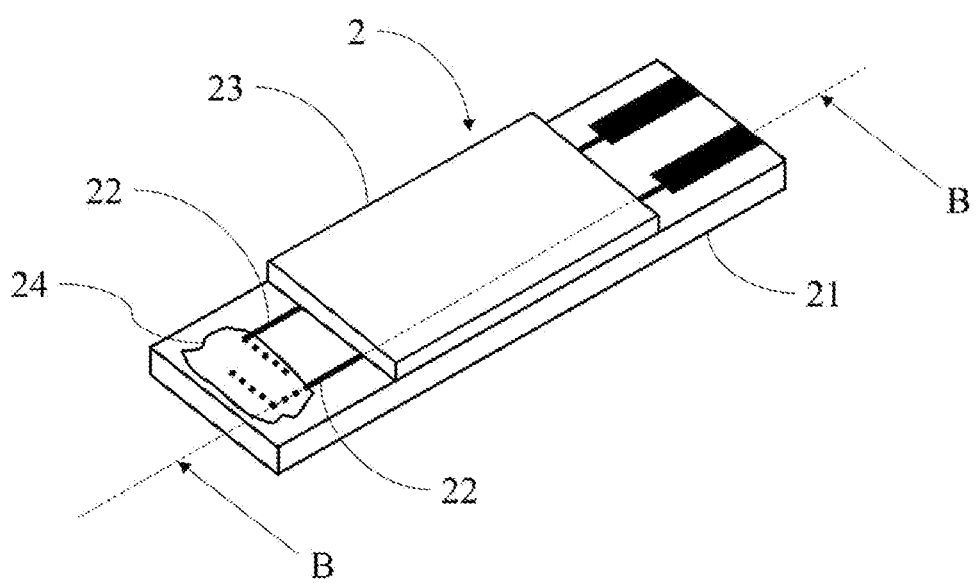
FIG. 2A is a schematic diagram representing an electrochemical strip according to a second embodiment of the present invention.

Referring to FIG. 2A, an electrochemical strip 2 according to a second embodiment of the invention includes a substrate 21, an electrode 22 disposed partly on the substrate 21, and an insulating layer 23 disposed partly on the electrode 22.

Figure 2B:
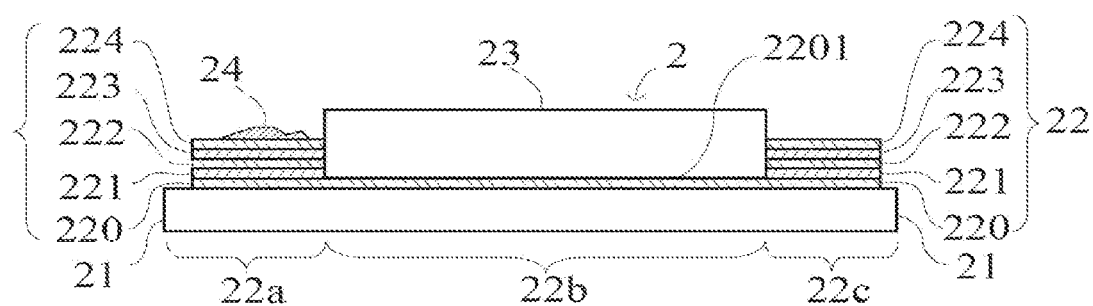
FIG. 2B is a cross-sectional view taken along B-B line of FIG. 2A, showing the electrochemical strip according to an example of the second embodiment of the present invention.

Referring to FIG. 2B, the insulating layer 23 is disposed partly on a region of the conductive paste layer 220 that excludes the electrode 22. In this embodiment of the present invention, the electrode 22 is partly formed on the substrate 21 such that the electrochemical strip 2 has a reacting region 22a, an inserting region 22c, and a conducting region 22b. The reacting region 22a is a region including only the conductive paste layer 220 and the electrode 22 and is used for an electrochemical reaction to be detected on the electrochemical strip 2, the conducting region 22b is a region including only the conductive paste layer 220 and the insulating layer 23 and is used for communication of an electrical signal resulted from the electrochemical reaction, and the inserting region 22c is a region including only the conductive paste layer 220 and the electrode 22 and is used for connecting with a bio-testing apparatus.

The reacting region 22a is coated with a substance 24 to be electrochemically reacting with an unknown sample to produce an electrical signal, and the electrical signal is transmitted and conducted through the conducting region 22b to the inserting region 22c. The conducting region 22b is served for communication of an electrical signal resulted from the electrochemical reaction between the reacting region 22a and the inserting region 22c. The inserting region 22c is served as the connecting region between the electrochemical strip 2 and the bio-testing apparatus. Actually, the electrical signal is transmitted from the inserting region 22c to the bio-testing apparatus to be converted to a corresponding information such as concentration of the unknown sample.

Referring to FIG. 2B, in an example of the embodiment, the conductive paste layer 220 is disposed on the substrate 21 firstly to be distributed on the reacting region 22a, the conducting region 22b, and the inserting region 22c. The conducting region 22b has only the conductive paste layer 220 and the insulating layer 23, while that the reacting region 22a and the inserting region 22c each has the conductive paste layer 220, the first metal layer 221, the second metal layer 222, the third metal layer 223, and the fourth metal layer 224.

Accordingly, a region including only the conductive paste layer 220, the first metal layer 221, the second metal layer 222, the third metal layer 223, and the fourth metal layer 224 is used as a region for an electrochemical reaction to be detected on the electrochemical strip, while a region including only the insulating layer and the conductive paste layer is used as a region for communicating a signal resulted from the electrochemical reaction.

The reacting region 22a is coated with a substance 24 to be reacted with an unknown sample via electrochemical reaction to produce an electrical signal to be transmitted to the inserting region 22c. Hence, the material used in the reacting region 22a should be a conductive metal with good conductivity, in order to reduce electrical resistance and Signal/Noise Ratio of the electrode 22, and to increase sensitivity and specificity of the electrochemical strip 2 during test. Moreover, since the inserting region 22c needs to transmit an electric signal to the bio-testing apparatus for calculation, the material used for the inserting region 22c should be a conductive metal with good conductivity, in order to have good sensitivity and specificity of the electrochemical strip 2 during test.

During manufacturing the electrochemical strip 2, the substrate 21 with printed conductive paste layer 220 is processed by plasma and acid-washing after the printing process of the conductive paste layer 220. The conducting region 22b used for communicating a signal resulted from the electrochemical reaction is further sprayed or coated with an insulating paint layer 2201. Due to the insulating paint layer 2201, the conducting region 22b never contacts with the reacting solution used in chemically plating during the following manufacturing steps. Apparently, the amount of several metals used in the first metal layer 221, the second metal layer 222, the third metal layer 223, and the fourth metal layer 224 is reduced effectively.

Figure 4A:
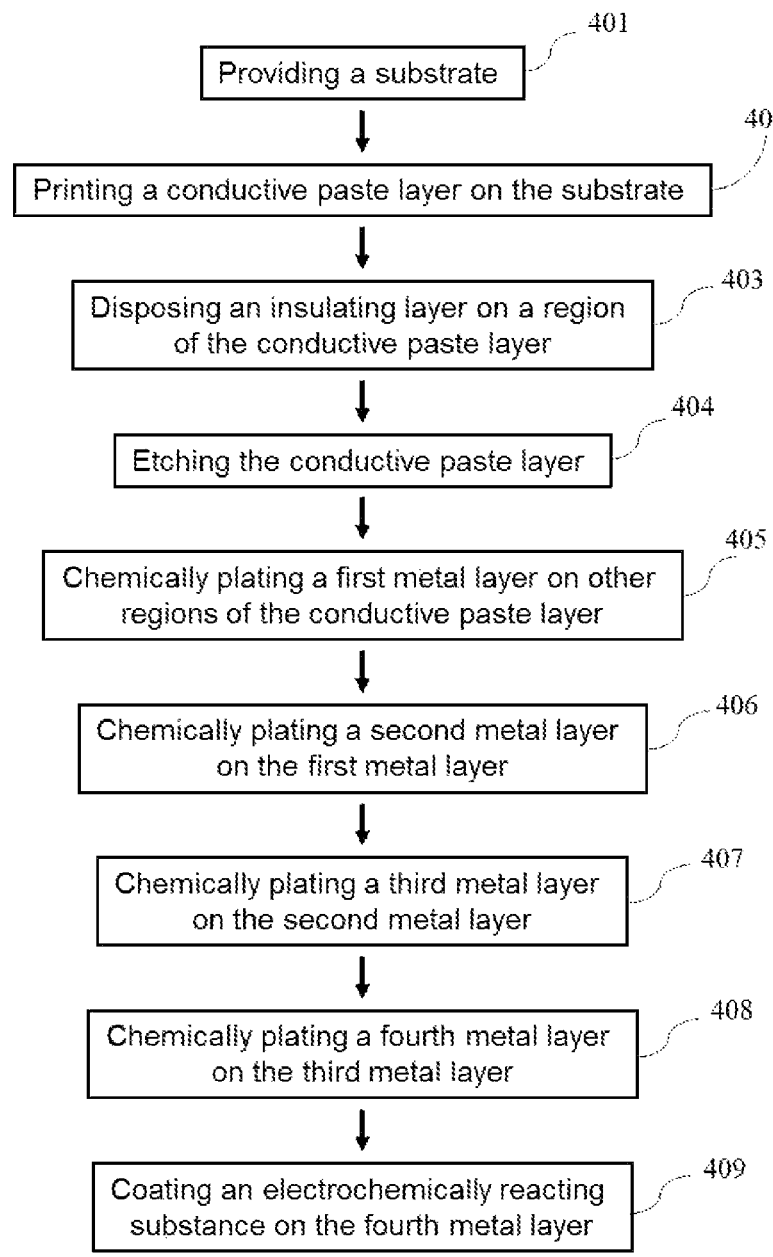
FIG. 4A is a flow chart illustrating steps of a manufacturing method of an electrochemical strip according to one example of a second embodiment of the present invention.

Referring to FIG. 4A, a manufacturing method of the electrochemical strip according to the first example of the second embodiment of the present invention includes the following steps:

Step 401: Providing a substrate 21. The material used for the substrate 11 can be bio-inert plastic such as polyethylene terephthalate (PET), polycarbonate (PC), polyimide, glass fiber or phenolic resin.

Step 402: Disposing an electrode layer 22 on the substrate 21, including the step of printing a conductive paste layer 220 on the substrate 21. The conductive paste layer 220 is made of a material selected from the group consisting of copper paste, nickel paste, silver paste, and silver-carbon paste.

Step 403: Coating an insulating paint layer 2201 and disposing an insulating layer 23 on a region 22b of the conductive paste layer 220, wherein the region 22b consisting of the insulating layer 23 and the conductive paste layer 220 is used for communicating a signal resulted from the electrochemical reaction.

Step 404: Etching the conductive paste layer 220, wherein the substrate 21 with the conductive paste layer 220 is etched by using plasma to eliminate the debris of the conductive paste layer 220, and then the surface of the conductive paste layer 220 is activated by acid-washing.

Step 405: Chemically plating a first metal layer 221 on other regions 22a and 22c other than the region 22b of the conductive paste layer 220, wherein the first metal layer is made of a group VIII metal.

Step 406: Chemically plating a second metal layer 222 on the first metal layer 221, wherein the second metal layer 222 is made of nickel (Ni).

Step 407: Chemically plating a third metal layer 223 on the second metal layer 222, wherein the third metal layer 223 is made of a group VIII metal.

Step 408: Chemically plating a fourth metal layer 224 on the third metal layer 223, wherein the fourth metal layer 224 is made of a material selected from the group consisting of palladium (Pd), gold (Au), and platinum (Pt).

Step 409: Coating an electrochemically reacting substance 24 on the fourth metal layer 224.

With respect to the first example of the second embodiment mentioned above, the disposition of the layering structure of the electrode 22 can be modified in order to reduce the manufacturing cost. Accordingly, in an another example of the second embodiment, an electrochemical strip is developed to have one side formed with only a carbon layer on a region of the conductive paste layer to save the cost of forming the first metal layer 221, the second metal layer 222, the third metal layer 223, and the fourth metal layer 224.

Figure 2C:
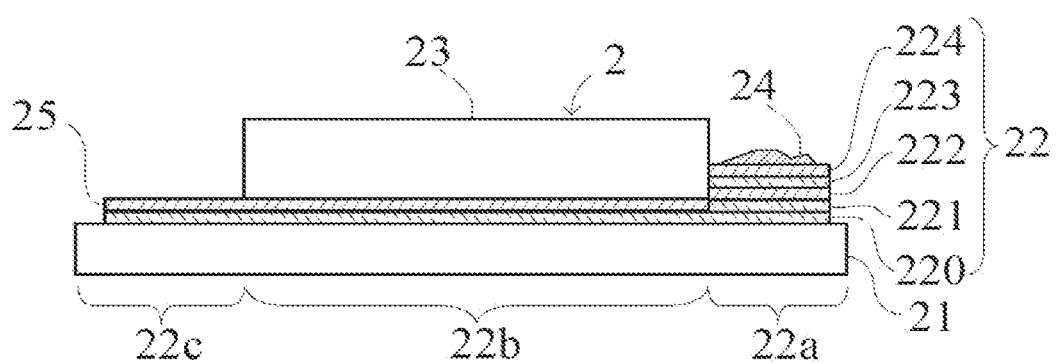
FIG. 2C is a cross-sectional view taken along B-B line of FIG. 2A, showing the electrochemical strip according to an another example of the second embodiment of the present invention.

Referring to FIG. 2C, a carbon layer 25 is printed partly on a region of the conductive paste layer 220. In this example, the electrochemical strip 2 is formed to have a reacting region 22a, an inserting region 22c, and a conducting region 22b, wherein the reacting region 22a is used for an electrochemical reaction to be detected on the electrochemical strip 2, the conducting region 22b is used for communication of an electrical signal resulted from the electrochemical reaction, and the inserting region 22c is used for connecting with a bio-testing apparatus.

Only the reacting region 22a is formed with the electrode 22 and is coated with a substance 24 to be electrochemically reacting with an unknown sample to produce an electrical signal, and the electrical signal is transmitted and conducted through the conducting region 22b to the inserting region 22c. The conducting region 22b is used for communication of an electrical signal resulted from the electrochemical reaction between the reacting region 22a and the inserting region 22c. The inserting region 22c is used as the connecting region between the electrochemical strip 2 and the bio-testing apparatus. Actually, the electrical signal is transmitted from the inserting region 22c to the bio-testing apparatus to be converted to get a corresponding information such as concentration of the unknown sample.

Referring to FIG. 2C, the conductive paste layer 220 is disposed on the substrate 21 firstly to be distributed on the reacting region 22a, the conducting region 22b and the inserting region 22c. Secondly, the carbon layer 25 is printed partly on the conductive paste layer 220 to be distributed on the conducting region 22b and the inserting region 22c. Hence, the inserting region 22c has only the conductive paste layer 220 and the carbon layer 25, the conducting region 22b has the conductive paste layer 220, the carbon layer 25, and the insulating layer 23, and the reacting region 22a has the conductive paste layer 220, the first metal layer 221, the second metal layer 222, the third metal layer 223, and the fourth metal layer 224.

Accordingly, the region including only the conductive paste layer 220, the first metal layer 221, the second metal layer 222, the third metal layer 223, and the fourth metal layer 224 is served as a region for an electrochemical reaction to be detected on the electrochemical strip, the region including only the insulating layer 23, the carbon layer 25, and the conductive paste layer 220 is served as a region for communicating a signal resulted from the electrochemical reaction, and the region including only the carbon layer 25 and the conductive paste layer 220 is served as a region for connecting the electrochemical strip 2 and the bio-testing apparatus.

The reacting region 22a is coated with a substance 24 to be reacted with an unknown sample via electrochemical reaction to produce an electrical signal to be transmitted to the inserting region 22c. Hence, the material used in the reacting region 22a should be a conductive metal with good conductivity, in order to reduce electrical resistance and Signal/Noise Ratio of the electrode 22, and to increase sensitivity and specificity of the electrochemical strip 2 during test. Moreover, since the inserting region 22c needs to transmit an electric signal to the bio-testing apparatus for calculation, the material carbon with good conductivity is chosen for the inserting region 22c in order to have good sensitivity and specificity of the electrochemical strip 2 during test. On the other hand, the manufacturing cost of using carbon in place of using several metals mentioned above is reduced.

During manufacturing the electrochemical strip 2 according to this example of the second embodiment of the present invention, chemically plating the first metal layer 221, the second metal layer 222, the third metal layer 223, and the fourth metal layer 224 on the inserting region 22c of the conductive paste layer 220 is replaced with printing the carbon layer 25. Apparently, the amount of several metals used in the first metal layer 221, the second metal layer 222, the third metal layer 223, and the fourth metal layer 224 is reduced more effectively.

Figure 4B:
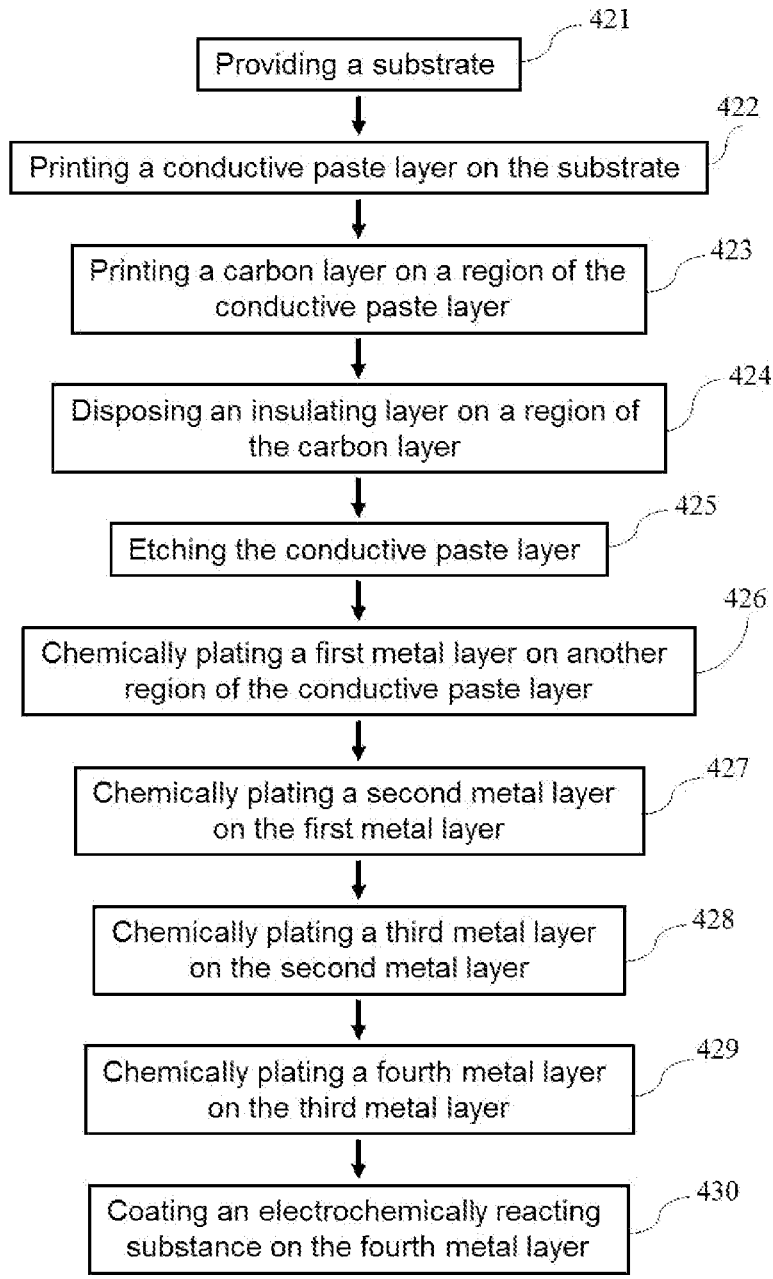
FIG. 4B is a flow chart illustrating steps of a manufacturing method of an electrochemical strip according to another one example of the second embodiment of the present invention.

Referring to FIG. 4B, a manufacturing method of the electrochemical strip according to this example of the second embodiment of the present invention includes the following steps:

Step 421: Providing a substrate 21. The material used for the substrate 11 can be bio-inert plastic such as polyethylene terephthalate (PET), polycarbonate (PC), polyimide, glass fiber or phenolic resin.

Step 422: Disposing an electrode layer 22 on the substrate 21, including the step of printing a conductive paste layer 220 on the substrate 21. The conductive paste layer 220 is made of a material selected from the group consisting of copper paste, nickel paste, silver paste, and silver-carbon paste.

Step 423: Printing a carbon layer 25 on the regions 22b and 22c other than the region 22a of the conductive paste layer 220.

Step 424: Disposing an insulating layer 23 on a region 22b of the carbon layer 25 such that the region 22b includes only the insulating layer 23, the carbon layer 25, and the conductive paste layer 220 and is used for communicating a signal resulted from the electrochemical reaction.

Step 425: Etching the conductive paste layer 220, wherein the substrate 11 with the conductive paste layer 220 is etched by using plasma to eliminate the debris of the conductive paste layer 220, and then the surface of the conductive paste layer 220 is activated by acid-washing.

Step 426: Chemically plating a first metal layer 221 on the region 22a of the conductive paste layer 220, wherein the first metal layer is made of a group VIII metal.

Step 427: Chemically plating a second metal layer 222 on the first metal layer 221, wherein the second metal layer 222 is made of nickel (Ni).

Step 428: Chemically plating a third metal layer 223 on the second metal layer 222, wherein the third metal layer 223 is made of a group VIII metal.

Step 429: Chemically plating a fourth metal layer 224 on the third metal layer 223, wherein the fourth metal layer 224 is made of a material selected from the group consisting of palladium (Pd), gold (Au) and platinum (Pt).

Step 430: Coating an electrochemically reacting substance 24 on the fourth metal layer 224.

Additionally, the substrate 21, the conductive paste layer 220, the first metal layer 221, the second metal layer 222, the third metal layer 223, and the fourth metal layer 224 said in the first and the second examples of the second embodiment, and the materials used therein, are almost the same as those said in the first embodiment, thus not described repeatedly here.

Furthermore, with respect to the first and second embodiments mentioned above, the disposition of the layering structure of the electrode 32 can be modified in order to effectively reduce the manufacturing cost again. Accordingly, in the third embodiment, an electrochemical strip 3 is developed to further replace the insulating layer and a part of the conductive paste layer with the carbon layer 35 and have only one region formed with the conductive paste layer 320 and the electrode 32 to more effectively save the manufacturing cost of the metals as well as reduce the environmental pollution resulted from the aforesaid manufacturing process.

Figure 5A:
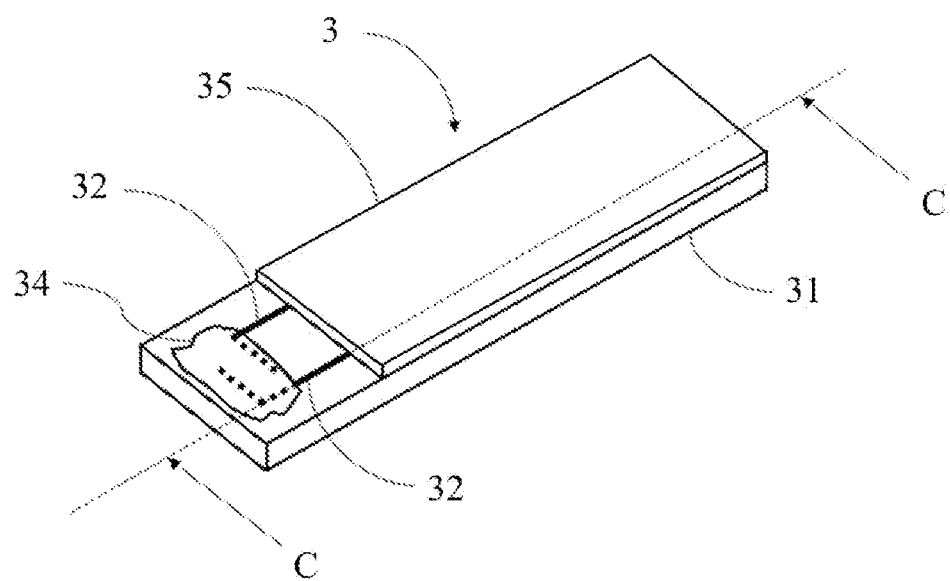
FIG. 5A is a schematic diagram representing an electrochemical strip according to a third embodiment of the present invention.

Referring to FIG. 5A, an electrochemical strip 3 according to a third embodiment of the invention includes a substrate 31, an electrode 32 disposed on one part of the substrate 31, and a carbon layer 35 disposed on another part of the substrate 31.

Figure 5B:
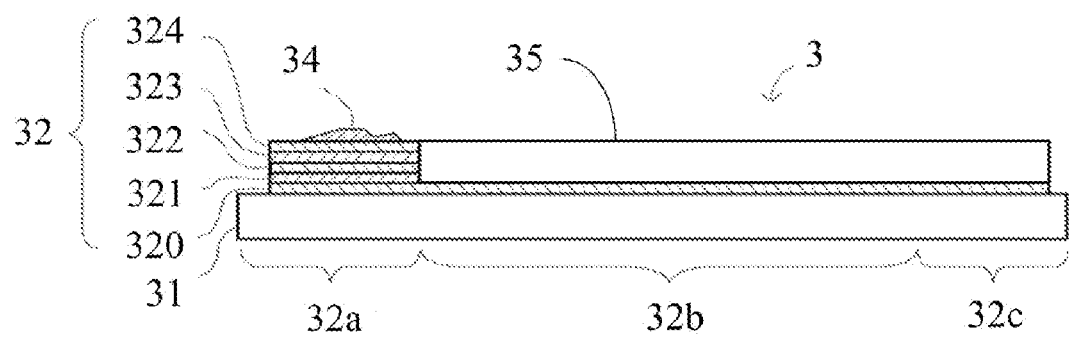
FIG. 5B is a cross-sectional view taken along C-C line of FIG. 5A, showing the electrochemical strip according to the third embodiment of the present invention.

Continually Referring to FIG. 5B, a cross-sectional view taken along C-C line of FIG. 5A, the carbon layer 35 is printed on two adjacent regions of the conductive paste layer 320 that excludes the electrode 32 as well as the electrode 32 is formed on the other region of the conductive paste layer 320 that excludes the carbon layer 35. Similar to the regional distribution of the substrate described in above-mentioned second embodiment, the electrochemical strip 3 has a reacting region 32a, an inserting region 32c, and a conducting region 32b. In detail, the reacting region 32a is a region including the conductive paste layer 320 and the electrode 32 and is used for an electrochemical reaction to be detected on the electrochemical strip 3, the conducting region 32b is a region including only the conductive paste layer 320 and the carbon layer 35 and is used for communication of an electrical signal resulted from the electrochemical reaction, and the inserting region 32c, as same as the conducting region 32b, is a region including only the conductive paste layer 320 and the carbon layer 35 and is used for connecting with a bio-testing apparatus.

In addition, only the reacting region 32a is formed with the electrode 32 and coated with a substance 34 to be electrochemically reacting with an unknown sample to produce an electrical signal, and the electrical signal is transmitted and conducted through the conducting region 32b to the inserting region 32c. The conducting region 32b is used for communication of an electrical signal resulted from the electrochemical reaction between the reacting region 32a and the inserting region 32c. The inserting region 32c is used as the connecting region between the electrochemical strip 3 and the bio-testing apparatus. In fact, the electrical signal is transmitted from the inserting region 32c to the bio-testing apparatus to be converted to a corresponding information such as concentration of the unknown sample.

Referring to FIG. 5B, the conductive paste layer 320 is disposed on the substrate 31 firstly to be distributed only on the reacting region 32a, the conducting region 32b and the inserting region 32c. Secondly, the carbon layer 35 is printed on the two adjacent regions other than the reacting region 32a to be distributed on the conducting region 32b and the inserting region 32c of the conductive paste layer 320. Also, the cover shape of the carbon layer 35 should be printed consistent with the conductive paste layer 320 as well as the width of the carbon layer 35 is printed slightly wider than that of the conductive paste layer 320 for completely covering the conductive paste layer 320. However, there is no insulating layer disposed on any region of the conductive paste layer 320 or the carbon layer 35. After that, the electrode 32 is thus only chemically plated on the reacting region 32a of the conductive paste layer 320. Namely, the conducting region 32b and the inserting region 32c each has only the conductive paste layer 320 and the carbon layer 35, while that the reacting region 32a has the conductive paste layer 320, the first metal layer 321, the second metal layer 322, the third metal layer 323, and the fourth metal layer 324.

Accordingly, a region including only the conductive paste layer 320, the first metal layer 321, the second metal layer 322, the third metal layer 323, and the fourth metal layer 324 is used as a region for an electrochemical reaction to be detected on the electrochemical strip, while a region including only the conductive paste layer 320 and the carbon layer 35 is used as a region for communicating a signal resulted from the electrochemical reaction as well as a region for connecting the electrochemical strip 3 and the bio-testing apparatus.

Similar to the manufacturing process and the material used in the second embodiment, the printed conductive paste layer 320 of the electrochemical strip 3 is also processed by plasma and acid-washing after the printing process of the conductive paste layer 320. Besides, the reacting region 32a is also coated with a substance 34 to be reacted with an unknown sample via electrochemical reaction to produce an electrical signal to be transmitted to the inserting region 32c. Accordingly, the material used in the reacting region 32a should be a conductive metal with good conductivity to reduce electrical resistance and Signal/Noise Ratio of the electrode 32 but increase sensitivity and specificity of the electrochemical strip 3 during test.

Notably, the printed conductive paste layer 320 is characterized by excellent effect of screen printing and promoting the subsequent electrochemical plating of the electrode 32, thus facilitating the production of a bio-test strip and saving the manufacturing cost. In addition, due to the unable replacement characteristic of the printed carbon layer 35, the conducting region 22b and the inserting region 32c will not be replaced by other materials with the reacting solution used in chemically plating during the following manufacturing steps. Moreover, the carbon layer 35 with good conductivity is printed partly on the conductive paste layer and displacing the insulating layer, thus providing good sensitivity and specificity for transmitting an electric signal to the bio-testing apparatus for calculation during test and further reducing the use of above-mentioned metals. Apparently, the amount of several metals used in the first metal layer 321, the second metal layer 322, the third metal layer 323, and the fourth metal layer 324 is reduced effectively, thereby achieving the purpose of lowering the manufacturing cost.

Figure 5C:
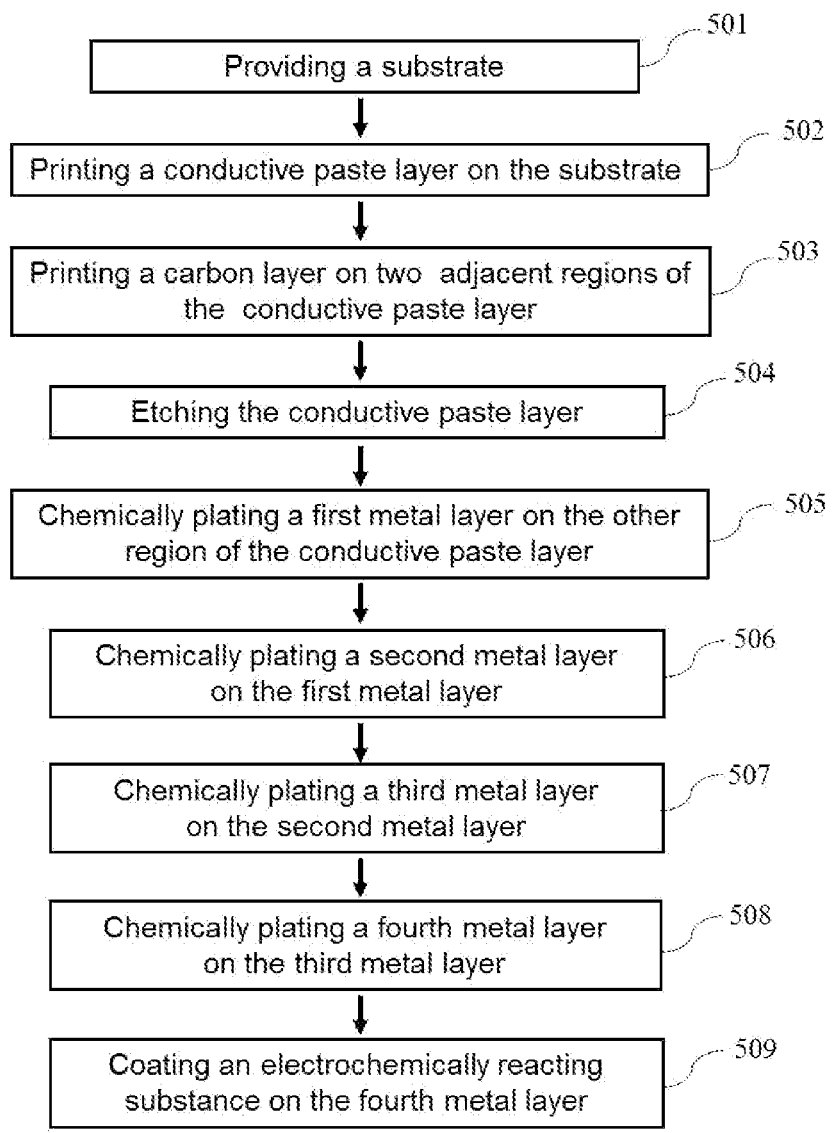
FIG. 5C is a flow chart illustrating steps of a manufacturing method of an electrochemical strip according to the third embodiment of the present invention.

Next, referring to FIG. 5C, a manufacturing method of the electrochemical strip according to the third embodiment of the present invention includes the following steps:

Step 501: Providing a substrate 31. The material used for the substrate 31 can be bio-inert plastic such as polyethylene terephthalate (PET), polycarbonate (PC), polyimide, glass fiber or phenolic resin.

Step 502: Disposing a conductive paste layer 320 on the substrate 21, including the step of printing a conductive paste layer 320 on the substrate 31. The conductive paste layer 320 is made of a material selected from the group consisting of copper paste, nickel paste, silver paste, and silver-carbon paste.

Step 503: Printing a carbon layer 35 on two adjacent regions 32b and 32c of the conductive paste layer 320, wherein the cover shape of the carbon layer 35 must be consistent with the conductive paste layer 320 and the width of the carbon layer 35 is printed slightly wider than that of the conductive paste layer 320. Namely, the regions 32b and 32c consisting of the carbon layer 35 and the conductive paste layer 320 are served for communicating a signal resulted from the electrochemical reaction and connecting with a bio-testing apparatus, respectively.

Step 504: Etching the conductive paste layer 320, wherein the substrate 31 with the conductive paste layer 320 is etched by using plasma to eliminate the debris of the conductive paste layer 320, and then the surface of the conductive paste layer 320 is activated by acid-washing.

Step 505: Chemically plating a first metal layer 321 on the region 32a other than two adjacent regions 32b and 32c of the conductive paste layer 320, wherein the first metal layer 321 is made of a group VIII metal.

Step 506: Chemically plating a second metal layer 322 on the first metal layer 321, wherein the second metal layer 322 is made of nickel (Ni).

Step 507: Chemically plating a third metal layer 323 on the second metal layer 322, wherein the third metal layer 323 is made of a group VIII metal.

Step 508: Chemically plating a fourth metal layer 324 on the third metal layer 323, wherein the fourth metal layer 324 is made of a material selected from the group consisting of palladium (Pd), gold (Au), and platinum (Pt).

Step 509: Coating an electrochemically reacting substance 34 on the fourth metal layer 324.

Similarly, the substrate 31, the conductive paste layer 320, the first metal layer 321, the second metal layer 322, the third metal layer 323, and the fourth metal layer 324 said in the third embodiment, and the materials used therein, are almost the same as those said in the first embodiment, thus not described repeatedly here.

In the first embodiment of the present invention, the electrochemical strip 1 includes a substrate 11, an electrode 12 disposed on the substrate 11, and an insulating layer 13 disposed on the electrode 12. The material used for substrate 11 can be bio-inert plastic such as polyethylene terephthalate (PET), polycarbonate (PC), polyimide, glass fiber or phenolic resin.

Additionally, the substrate 11 with the conductive paste layer 120 is immersed in a first electrolytic solution containing the group VIII metal ions before plating the first metal layer 121, wherein the first electrolytic solution not only controls the electrolytic temperature and time but also adjusts the ion concentration of the group VIII metal and appropriate pH level in the first electrolytic solution.

The immersing process used for chemically plating the first metal layer 121 is also used for chemically plating the second metal layer 122, the third metal layer 123, and the fourth metal layer 124. However, the electrolytic solution used in chemically plating the first metal layer 121 is different from that used in plating the second metal layer 122, the third metal layer 123, and the fourth metal layer 124. For example, the substrate 11 plated with the first metal layer 121 is immersed in a second electrolytic solution containing nickel (Ni) ions to plate the second metal layer 122 on the first metal layer 121.

By the same way, the substrate 11 plated with the first metal layer 121 and the second metal layer 122 is immersed in a third electrolytic solution containing the group VIII metal ions to plate the third metal layer 123 on the second metal layer 122; the substrate 11 plated with the first metal layer 121, the second metal layer 122, and the third metal layer 123, is immersed in a fourth electrolytic solution containing the group VIII metal ions selected from palladium (Pd) ion, gold (Au) ion, and platinum (Pt) ion to plate the fourth metal fourth layer 124 on the third metal layer 123.

Moreover, as the role of the first electrolytic solution in chemically plating, the second electrolytic solution, the third electrolytic solution, and the fourth electrolytic solution not only control the electrolytic temperature and time, but also adjust the ion concentration of metals and appropriate pH level in the electrolytic solution mentioned above.

The present invention is disclosed above by preferred embodiments. However, persons skilled in the art should understand that the preferred embodiments are illustrative of the present invention only, but should not be interpreted as restrictive of the scope of the present invention. Persons skilled in the art are able to understand and implement the above disclosure of the present invention. Hence, all equivalent changes or modifications made to the aforesaid embodiments without departing from the spirit embodied in the present invention should fall within the scope of the present invention.

What is claimed is:

1. An electrochemical strip, comprising:
   a substrate;
   a printed conductive paste layer disposed on the substrate;
   printed carbon layer disposed on a first region of the conductive paste layer;
   a first metal layer disposed on the conductive paste layer on a second region excluding the first region of the conductive paste layer;
   a second metal layer disposed on the first metal layer;
   a third metal layer disposed on the second metal layer; and
   a fourth metal layer disposed on third metal layer;
   wherein the first metal layer is made of a group VIII metal, the second metal layer is made of nickel (Ni), the third metal layer is made of a group VIII metal, and the fourth metal layer made of a metal selected from the group consisting of palladium (Pd), gold (Au) and platinum (Pt).

2. The electrochemical strip as recited in claim 1, wherein the substrate is made of a material selected from the group consisting of polyethylene terephthalate (PET), polycarbonate (PC), polyimide, glass fiber and phenolic resin.

3. The electrochemical strip as recited in claim 1, wherein the conductive paste layer is made of a material selected from the group consisting of copper paste, nickel paste, silver paste, and silver carbon paste.

4. The electrochemical strip as recited in claim 1, wherein the first metal layer is made of palladium (Pd).

5. The electrochemical strip as recited in claim 1, wherein the third metal layer is made of palladium (Pd).

6. The electrochemical strip as recited in claim 1, wherein the fourth metal layer is made of gold (Au).

7. The electrochemical strip as recited in claim 1, wherein the fourth metal layer is made of palladium (Pd).

8. The electrochemical strip as recited in claim 1, wherein a material is coated on the first region consisting of the conductive paste layer, the first metal layer, the second metal layer, the third metal layer, and the fourth metal layer.

9. The electrochemical strip as recited in claim 1, wherein the second region consisting of conductive paste layer, the first metal layer, the second metal layer, the third metal layer, and the fourth metal layer is used as a region for an electrochemical reaction to be detected on the electrochemical strip, and the first region consisting of the conductive paste layer and the carbon layer is used as a region for communicating a signal resulted from the electrochemical reaction and a region for connecting the electrochemical strip and the bio-testing apparatus.

10. The electrochemical strip as recited in claim 9, wherein a substance for the electrochemical reaction is coated on the second region.

* * * * *